(12) United States Patent
Isogai et al.

(10) Patent No.: US 7,430,904 B2
(45) Date of Patent: Oct. 7, 2008

(54) CAPACITIVE HUMIDITY SENSOR AND METHOD OF MANUFACTURING THE SAME

(75) Inventors: Toshiki Isogai, Nagoya (JP); Toshikazu Itakura, Toyota (JP)

(73) Assignees: DENSO CORPORATION, Kariya (JP); Nippon Soken, Inc., Nishio (JP)

( * ) Notice: Subject to any disclaimer, the term of this patent is extended or adjusted under 35 U.S.C. 154(b) by 345 days.

(21) Appl. No.: 11/265,280

(22) Filed: Nov. 3, 2005

(65) Prior Publication Data
US 2006/0096371 A1 May 11, 2006

(30) Foreign Application Priority Data
Nov. 9, 2004 (JP) .............................. 2004-325519

(51) Int. Cl.
*G01N 27/22* (2006.01)
(52) U.S. Cl. ..................................... 73/335.04; 73/23.2
(58) Field of Classification Search .............. 73/335.04, 73/23.2; 438/96, 97, 379, 482, 488
See application file for complete search history.

(56) References Cited

U.S. PATENT DOCUMENTS 5,050,434 A * 9/1991 Demisch .................. 73/335.04
6,580,600 B2 6/2003 Toyoda et al.
2002/0114125 A1 8/2002 Toyoda et al.
2002/0142478 A1* 10/2002 Wado et al. .................. 436/151
2003/0179805 A1 9/2003 Hamamoto et al.

FOREIGN PATENT DOCUMENTS

JP          01156655 A   *  6/1989
JP       20002005867 A   *  1/2002

* cited by examiner

*Primary Examiner*—Hezron E. Williams
*Assistant Examiner*—Rodney T Frank
(74) *Attorney, Agent, or Firm*—Posz Law Group, PLC

(57) ABSTRACT

A capacitive humidity sensor includes a semiconductor substrate, a protective layer and a humidity sensitive section including a pair of comb electrodes and a humidity sensitive layer having a dielectric constant, which changes in accordance with humidity. The comb electrodes are disposed on one surface of the semiconductor substrate through the protective layer to face each other with a predetermined gap. An interface between the protective layer and the humidity sensitive layer is planarized so that the sensor prevents a hysteresis in a variation of capacitance. For example, a surface of the protective layer can be made flat by polishing.

11 Claims, 5 Drawing Sheets

CAPACITIVE HUMIDITY SENSOR AND METHOD OF MANUFACTURING THE SAME

CROSS REFERENCE TO RELATED APPLICATION

This application is based on Japanese Patent Application No. 2004-325519 filed on Nov. 9, 2004, the disclosure of which is incorporated herein by reference.

FIELD OF THE INVENTION

The present invention relates to a capacitive humidity sensor having a humidity sensitive section and a method of manufacturing the sensor.

BACKGROUND OF THE INVENTION

A capacitive humidity sensor having a humidity sensitive section including a pair of comb electrodes covered with a humidity sensitive layer through a protective layer, and a method of manufacturing the sensor are disclosed in, for example, U.S. Pat. No. 6,580,600 corresponding to JP-A-2002-243690.

FIGS. 5A to 5C show a capacitive humidity sensor 100 disclosed in U.S. Pat. No. 6,580,600. The sensor 100 includes a humidity sensitive section 10 and a circuit element section 20. The humidity sensitive section 10 includes a comb type capacitive element having a pair of comb electrodes 10a, 10b. The comb electrodes 10a, 10b are formed on one surface of a semiconductor substrate 1 through an insulating layer 2 to face each other with a predetermined gap, so that comb-teeth portions of the comb electrodes 10a, 10b are alternately arranged. The circuit element section 20 includes a reference capacitance section 21 and a signal processing circuit section 22. The reference capacitance section 21 includes a stacked type capacitive element having stacked electrodes and the insulating layer 2 as a dielectric.

The comb electrodes 10a, 10b are made of aluminum (Al) or aluminum alloy. The comb electrodes 10a, 10b are formed in the same process as wiring of a semiconductor element, which is formed at a different position of the substrate 1, is performed. Therefore, the comb electrodes 10a, 10b can be formed while the wiring is performed. A humidity sensitive layer 4 covers the comb electrodes 10a, 10b through a protective layer 3. The humidity sensitive layer 4 has a dielectric constant, which changes in accordance with a change in relative humidity. The protective layer 3 is made of silicon oxide ($SiO_2$), silicon nitride ($Si_3N_4$), or a laminated member of silicon oxide and silicon nitride. The protective layer 3 protects the comb electrodes 10a, 10b from deterioration such as corrosion. As shown in FIG. 5A, the protective layer 3 of the humidity sensitive section 10 is a part of a protective layer covering all over a surface of the substrate 1. Therefore, the protective layer 3 of the humidity sensitive section 10 is formed while the protective layer of the substrate 1 is formed. The humidity sensitive layer 4 is made of polyimide resin, for example.

The humidity sensitive layer 4 has a relative permittivity of about 3 to 4, whereas water ($H_2O$) has a relative permittivity of about 80. Therefore, when water molecule is absorbed in the humidity sensitive layer 4, the dielectric constant of the humidity sensitive layer 4 increases. Accordingly, the capacitance of the humidity sensitive section 10 increases. Thus, the dielectric constant of the humidity sensitive layer 4 changes in accordance with a change in the relative humidity in the ambient atmosphere, and accordingly the capacitance of the humidity sensitive section 10 changes.

In contrast, the capacitance of the reference capacitance section 21 remains constant, even when the relative humidity in the ambient atmosphere changes. That is because the reference capacitance section 21 is not covered with the humidity sensitive layer 4.

The comb type capacitive element of the humidity sensitive section 10 is connected in series with the stacked type capacitive element of the reference capacitance section 21. Therefore, the capacitance change of the humidity sensitive section 10 can be detected as a variation of a ratio between voltages applied to the respective capacitive elements. Then, the relative humidity is calculated in the signal processing circuit section 22 based on the detected variation of the ratio between the voltages. Thus, the sensor 100 measures the relative humidity in the atmosphere. The signal processing circuit section 22 is integrally provided in the sensor 100 so that the sensor 100 has a small size and is manufactured at low cost.

However, as disclosed in US 2003/0179805A1 corresponding to JP-A-2003-270189, it has been showed that the sensor 100 exhibited hysteresis in a variation of capacitance. The hysteresis of the sensor 100 means a difference of the amount of change in capacitance of the humidity sensitive section 10 between during an increase in relative humidity and during a decrease in relative humidity. It has been considered that the hysteresis was caused due to grooves 3m in the protective layer 3. Specifically, it is difficult for the water absorbed in the humidity sensitive layer 4 located inside the grooves 3m to move (evaporate) when the relative humidity decreases, because the grooves 3m become narrower toward the top. As a result, the change in the capacitance of the humidity sensitive section 10 is delayed than the change in the relative humidity.

In a capacitive humidity sensor disclosed in US 2003/0179805A1 corresponding to JP-A-2003-270189, a separation distance between adjacent comb teeth portions of a pair of comb electrodes is widened in order to prevent the hysteresis. In this case, water absorbed in a humidity sensitive layer can easily move and the hysteresis can be reduced. However, when the separation distance between the adjacent comb teeth portions is widened, electrode density per unit area decreases. Therefore, a capacitance between the comb electrodes decreases, and sensitivity of the humidity sensitive section decreases.

SUMMARY OF THE INVENTION

In view of the above-described problem, it is an object of the present invention to provide a capacitive humidity sensor that prevents hysteresis in a variation of capacitance without a reduction in sensitivity, and a method of manufacturing the sensor.

According to an aspect of the present invention, a capacitive humidity sensor includes a semiconductor substrate, a protective layer, a pair of comb electrodes disposed on a surface of the semiconductor substrate to face each other with a predetermined gap, and a humidity sensitive layer having a dielectric constant, which changes in accordance with humidity.

In the sensor, the humidity sensitive layer covers the comb electrodes through the protective layer, and an interface between the protective layer and the humidity sensitive layer is made flat. Therefore, there is no groove in a surface of the protective layer. Thus, water absorbed in the humidity sensitive layer can move (evaporate) easily, even when relative humidity decreases. Accordingly, capacitance of a humidity sensitive section constructed with the humidity sensitive layer and the comb teeth portions changes in accordance with a change in the relative humidity without a delay, even when the relative humidity decreases. As a result, hysteresis in a variation of capacitance can be effectively prevented.

Further, a separation distance between adjacent comb teeth portions of the comb electrodes can be adjusted to a desired value, so that the capacitance of the humidity sensitive section can be adjusted to a desired value. Therefore, reduction in the sensitivity of the humidity sensitive section can be prevented.

Accordingly, the sensor can prevent the hysteresis while preventing the reduction in the sensitivity of the humidity sensitive section.

An insulating layer can be disposed on the substrate. In this case, the comb electrodes can be embedded in the insulating layer. Further, the comb electrodes can be made of aluminum or aluminum alloy, and the protective layer can be made of silicon oxide, silicon nitride, or a laminated member of a silicon oxide layer and a silicon nitride layer. Furthermore, the humidity sensitive layer can be made of polyimide resin.

Alternatively, the comb electrodes can be arranged on the insulating layer and embedded in the protective layer.

According to another aspect of the present invention, a method of manufacturing a capacitive humidity sensor includes steps of forming a pair of comb electrodes arranged on a surface of a semiconductor substrate to face with each other with a predetermined gap, forming a protective layer to protect the comb electrodes, and forming a humidity sensitive layer which contacts a surface of the protective layer and covers the comb electrodes through the protective layer. In this method, the forming of the protective layer includes a step of polishing the surface of the protective layer to be flat. Therefore, the interface between the protective layer and the humidity sensitive layer can be easily made flat.

The method can be further provided with a step of forming an insulating layer on the surface of the semiconductor substrate. In this case, the comb electrodes can be formed directly on the insulating layer.

According to further another aspect of the present invention, a method of manufacturing a capacitive humidity sensor includes steps of forming an insulating layer on a surface of a semiconductor substrate, forming a pair of comb electrodes to be embedded in the insulating layer so as to form a flat surface, forming a protective layer on the flat surface to protect the comb electrodes, and forming a humidity sensitive layer which covers the comb electrodes through the protective layer. Even in this case, the interface between the protective layer and the humidity sensitive layer can be easily made flat.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS

Figure 1A:
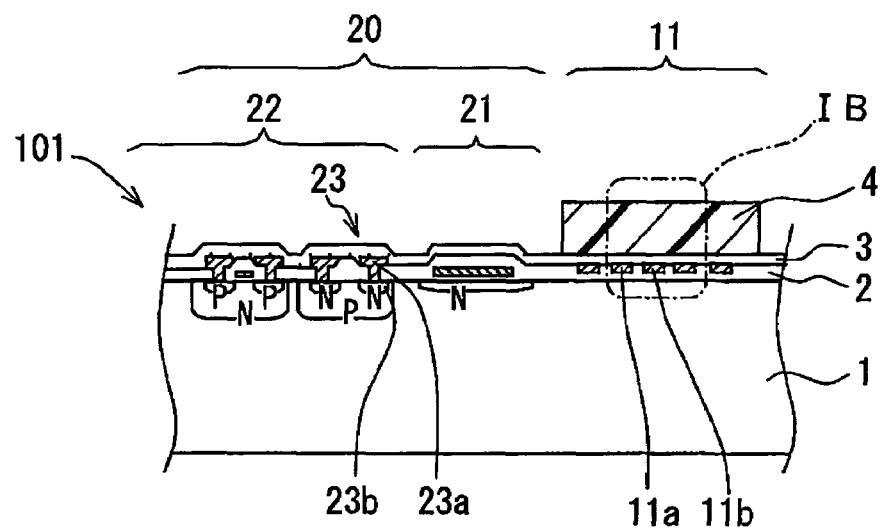
FIG. 1A is a schematic cross-sectional view showing a part of a capacitive humidity sensor according to an embodiment of the present invention.
Figure 1B:
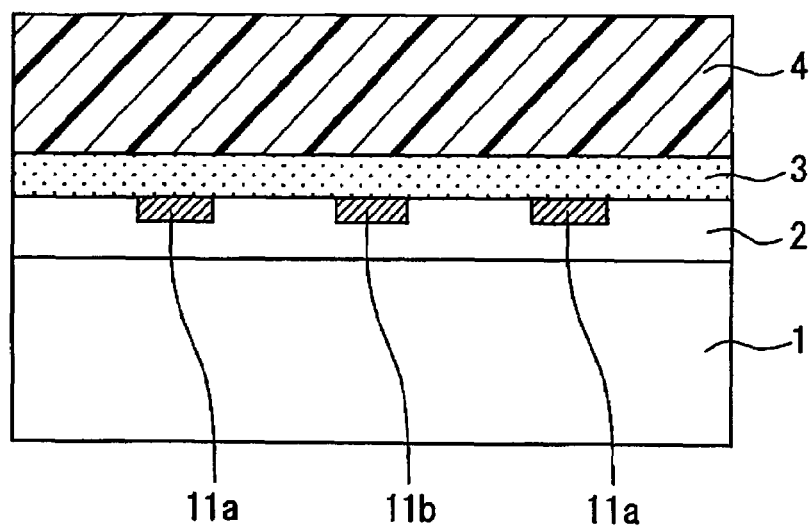
FIG. 1B is an enlarged view of a portion 1B in FIG. 1A.

FIGS. 1A and 1B show a capacitive humidity sensor 101 according to an embodiment of the present invention. The sensor 101 includes a humidity sensitive section 11 and a circuit element section 20.

The circuit element section 20 includes a reference capacitance section 21 and a signal processing circuit section 22. The reference capacitance section 21 is a stacked type capacitive element having an insulating layer 2 as a dielectric. The insulating layer 2 is disposed on a semiconductor substrate 1.

The humidity sensitive section 11 includes a comb type capacitive element having a pair of comb electrodes 11a, 11b. The comb electrodes 11a, 11b are formed on one surface of the substrate 1 through an insulating layer 2 to face each other with a predetermined gap, so that adjacent comb teeth portions of the respective comb electrodes 11a, 11b are alternately arranged. A humidity sensitive layer 4 covers the comb electrodes 11a, 11b through a protective layer 3.

Figure 5A:
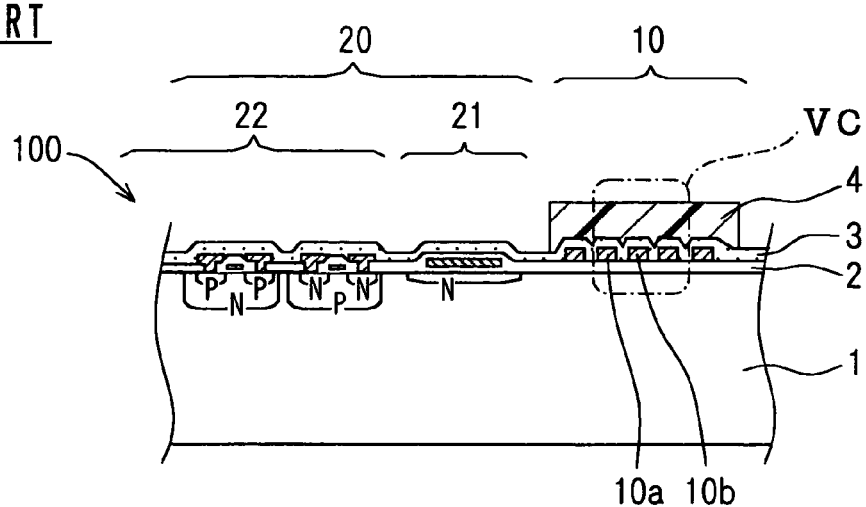
FIG. 5A is a cross-sectional view showing a part of a capacitive humidity sensor according to prior art.
Figure 5B:
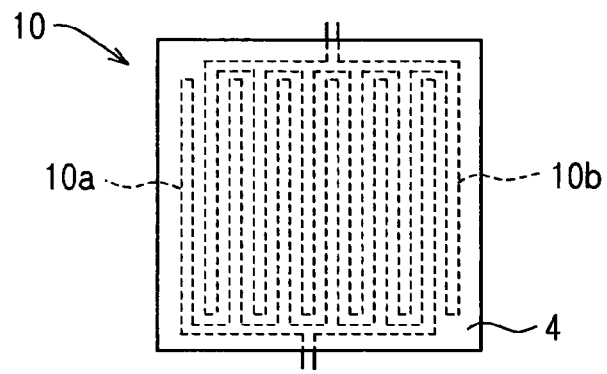
FIG. 5B is a top view of a humidity sensitive section of the sensor in FIG. 5A.
Figure 5C:
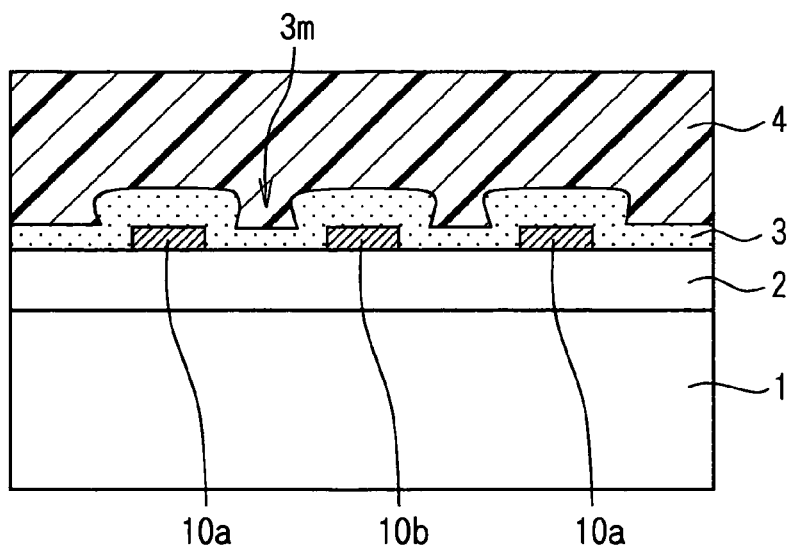
FIG. 5C is an enlarged view of a portion VC in FIG. 5A.

As shown in FIG. 1B, the comb electrodes 11a, 11b are embedded in the insulating layer 2. Thus, a surface of the protective layer 3 is planarized so that an interface between the protective layer 3 and the humidity sensitive layer 4 becomes flat. Therefore, there is no groove 3m in the protective layer 3 of the sensor 101, in contrast to the sensor 100 shown in FIG. 5C.

The sensor 101 can detect relative humidity in the atmosphere. Specifically, a change in capacitance of the humidity sensitive section 11 is detected as a variation of a ratio between voltages applied to the respective capacitive elements of the humidity sensitive section 11 and the reference capacitance section 21. Then, the relative humidity is calculated in the signal processing circuit section 22 based on the detected variation of the ratio between the voltages. The signal processing circuit section 22 is integrally provided in the sensor 101 so that the sensor 101 can have a small size.

As described above, in the sensor 100 shown in FIGS. 5A to 5C, it is difficult for water absorbed in the humidity sensitive layer 4 located inside the grooves 3m to move (evaporate), when relative humidity decreases. As a result, the capacitance change of the humidity sensitive section 10 is delayed than the relative humidity change, when the relative humidity decreases.

In contrast, in the sensor 101 of the present embodiment, the interface between the protective layer 3 and the humidity sensitive layer 4 is made flat so that there is no groove in the protective layer 3. Therefore, water absorbed in the humidity sensitive layer 4 can move (evaporate) easily, even when relative humidity decreases. The capacitance of the humidity capacitive section 11 changes in accordance with the change in the relative humidity without a delay. Thus, the sensor 101 prevents the hysteresis from being caused.

Further, in the sensor 101, a separation distance between the adjacent comb teeth potions of the comb electrodes 11a, 11b can be adjusted to a desired value, so that the capacitance of the humidity sensitive section can be adjusted to a desired value. Therefore, reduction in sensitivity of the humidity sensitive section 11 can be prevented.

Thus, even when the sensor 101 has the comb electrodes 11a, 11b, which are covered by the humidity sensitive layer 4 through the protective layer 3, the sensor 101 can prevent the hysteresis while preventing the reduction in the sensitivity of the humidity sensitive section 11.

The comb electrodes 11a, 11b can be made of aluminum (Al) or aluminum alloy, which is generally used as a wiring material for a semiconductor device. The comb electrodes 11a, 11b can be formed in the same process as a wiring 23a of a semiconductor element 23, which is formed at a different position in the substrate 1. Therefore, the comb electrodes 11a, 11b can be easily provided while the wiring 23a of the semiconductor element 23 is formed. The protective layer 3 can be made of silicon oxide, silicon nitride, or a laminated member of a silicon oxide layer and a silicon nitride layer, which is generally used as a material for forming a protective layer of a semiconductor device.

The protective layer 3 of the humidity sensitive section 11 can be a protective layer covering over all the surface of the substrate 1 including the wiring of the semiconductor element. In other words, a part of the protective layer of the substrate 1 can be used as the protective layer 3. In this case, the protective layer 3 can be formed in the same process as the protective layer of the substrate 1, so that manufacturing cost of the sensor 101 can be reduced.

Further, the humidity sensitive section 11 and the circuit element section 20 including the signal processing circuit section 22 are integrally provided in the sensor 101. Therefore, the sensor 101 has a small size and can be manufactured at low cost.

Manufacturing processes of the humidity sensitive section 11 of the sensor 101 will be described with reference to FIGS. 2A to 2E.

Figure 2A:
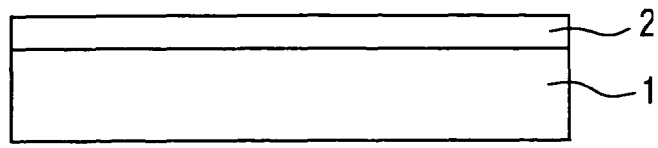
FIGS. 2A to 2E are cross-sectional views showing a manufacturing process of a humidity sensitive section of the sensor in FIG. 1A.

Referring to FIGS. 1A and 2A, a silicon semiconductor substrate 1 is prepared. An insulating layer 2 made of silicon oxide is formed on the substrate 1. A diffusion layer 23b of a semiconductor element 23 that constructs the circuit section 20 is formed in the substrate 1. The insulating layer 2 is provided as an interlayer insulation layer that is used for forming the wiring 23a of the diffusion layers 23b.

Figure 2B:
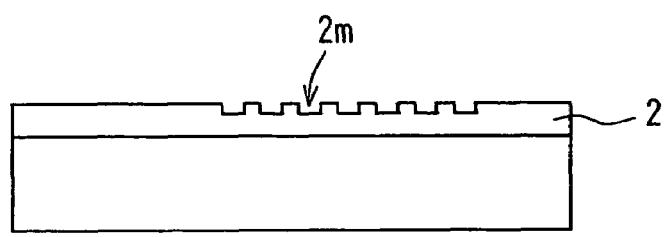

Referring to FIG. 2B, grooves 2m are formed in the insulating layer 2 by etching, after an anneal process is applied to the substrate 1. A pattern and a thickness of the grooves 2m are set so that comb electrodes 11a, 11b having a predetermined pattern and thickness are fitted into the grooves 2m.

Figure 2C:
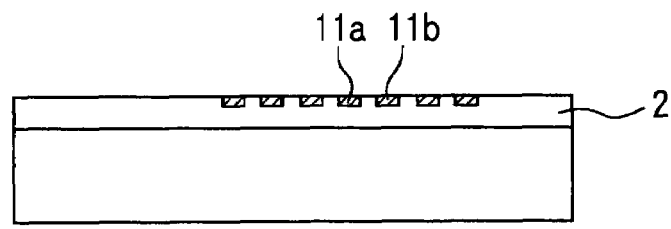

Referring to FIG. 2C, the grooves 2m are filled with a wiring material such as aluminum or aluminum alloy to form the comb electrodes 11a, 11b. As an example, the wiring material is formed over all the surface of the substrate 1 by evaporation, for example. Then, an unnecessary wiring material is removed by etching so that the comb electrodes 11a, 11b are formed. Alternatively, after the wiring material is formed, the wiring material is etched back by Chemical Mechanical Polishing (CMP), for example. Consequently, the wiring material is left only in the grooves 2m so that the comb electrodes 11a, 11b are formed. Thus, the surface of the insulating layer 2 including the comb electrodes 11a, 11b can be made flat.

Figure 2D:
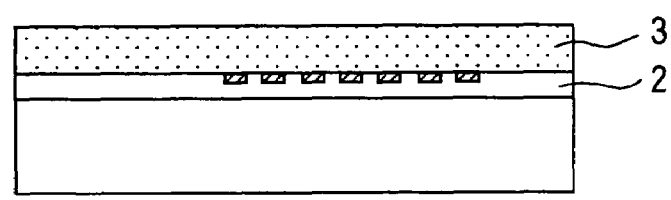

Referring to FIG. 2D, a protective layer 3 is formed on the insulating layer 2 where the comb electrodes 11a, 11b are embedded. The protective layer 3 is made of silicon oxide or silicon nitride, for example. The surface of the protective layer 3 becomes flat, because the surface of the insulating layer 2, contacting the protective layer 3 is made flat. The protective layer 3 can be formed in the same process as a protective layer covering the substrate 1 including the wiring of the semiconductor element. In this case, manufacturing cost of the sensor 101 can be reduced.

Figure 2E:
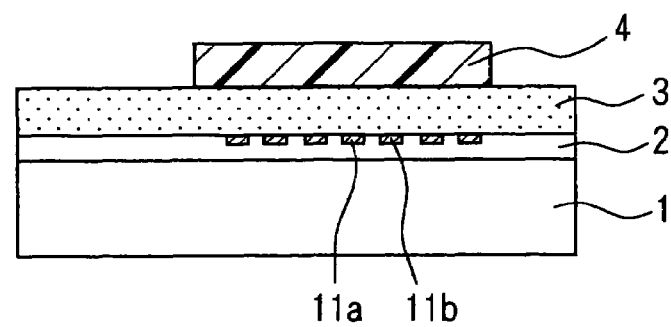

Referring to FIG. 2E, a humidity sensitive layer 4 made of polyimide resin is formed on the protective layer 3. Specifically, polyimide resin is applied to the protective layer 3 and burned. Then, the humidity sensitive layer 4 is formed by patterning the polyimide resin. An interface between the protective layer 3 and the humidity sensitive layer 4 becomes flat, because the surface of the protective layer 3 is made flat.

Through the steps shown in FIGS. 2A to 2E, the humidity sensitive section 11 of the sensor 101 is formed.

Figure 3A:
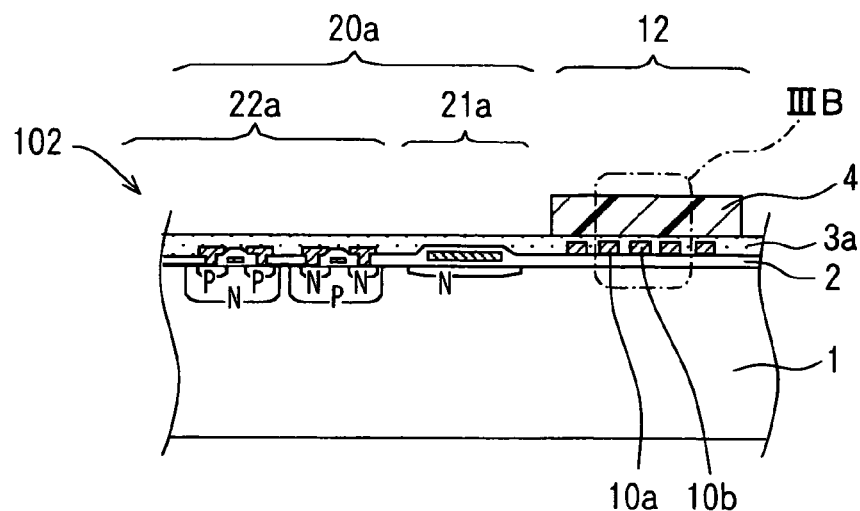
FIG. 3A is a cross-sectional view showing a part of a capacitive humidity sensor according to a modification of the sensor in FIG. 1A.
Figure 3B:
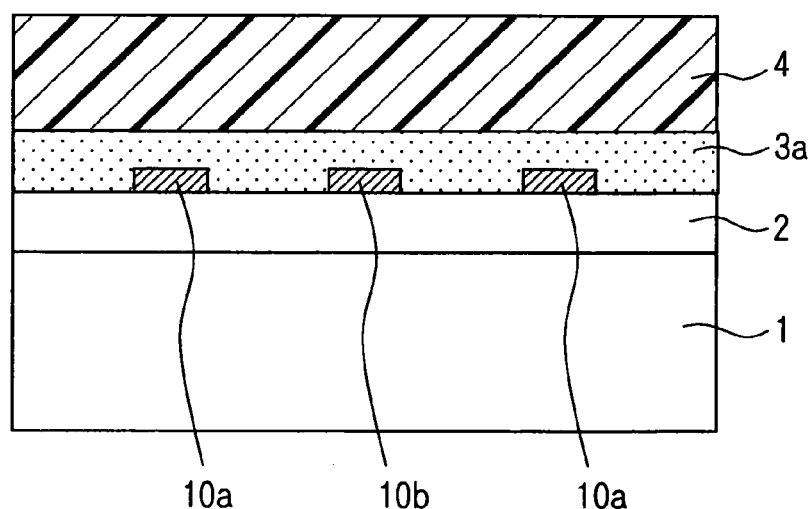
FIG. 3B is an enlarged view of a portion IIB in FIG. 3A.

FIGS. 3A and 3B show a capacitive humidity sensor 102 according to a modification of the sensor 101. The sensor 102 includes a humidity sensitive section 12 and a circuit element section 20a.

The circuit element section 20a includes a reference capacitance section 21a and a signal processing circuit section 22a. The reference capacitance section 21a is a staked type capacitive element having an insulating layer 2 as a dielectric. The insulating layer 2 is disposed on a semiconductor substrate 1.

The humidity sensitive section 12 includes a comb type capacitive element having a pair of comb electrodes 10a, 10b and a humidity sensitive layer 4 made of polyimide resin. The comb electrodes 10a, 10b are formed on one surface of the semiconductor substrate 1 through the insulating layer 2 to face each other with a predetermined gap, so that comb teeth portions of the respective comb electrodes 10a, 10b are alternatively arranged. A protective layer 3a is disposed on the comb electrodes 10a, 10b.

In this way, the sensor 102 shown in FIGS. 3A and 3B has a similar basic structure as the sensor 101 shown in FIGS. 1A and 1B. However, the protective layer 3a of the sensor 102 is thick enough to be planarized by means of polishing. In the sensor 102, after a surface of the protective layer 3a is polished and planarized, the humidity sensitive layer 4 is disposed to cover the comb electrodes 10a, 10b through the protective layer 3a. Therefore, an interface between the protective layer 3a and the humidity sensitive layer 4 becomes flat, and there is no groove in the protective layer 3a.

The signal processing circuit section 22a is integrally provided in the sensor 102 so that the sensor 102 has a small size. Further, there is no groove in the protective layer 3a because of the flat interface between the protective layer 3a and the humidity sensitive layer 4. In the sensor 102, therefore, hysteresis, i.e., a difference of the amount of change in capacitance of the humidity sensitive section 12 between during an increase in relative humidity and during a decrease in relative humidity is prevented.

Furthermore, a separation distance between the adjacent comb teeth portions of the comb electrodes 10a, 10b can be adjusted to a desired value, so that the capacitance of the humidity sensitive section 12 can be adjusted to a desired value. Therefore, reduction in sensitivity of the humidity sensitive section 12 can be prevented.

The protective layer 3a can be made of silicon oxide or silicon nitride, which is generally used as a material for manufacturing a semiconductor device. The protective layer 3a of the humidity sensitive section 12 can be a protective layer covering over all the surface of the substrate 1 including a wiring of a semiconductor element. In other words, a part of the protective layer of the substrate 1 can be used as the protective layer 3a of the humidity sensitive section 12. In this case, the protective layer 3a can be formed in the same process where the protective layer of the substrate 1 is formed, so that manufacturing cost of the sensor 102 can be reduced.

Thus, the sensor 102 can prevent the hysteresis while preventing a reduction in sensitivity of the humidity sensitive section 12. Further, the sensor 102 has a small size and can be manufactured at low cost.

Manufacturing processes of the humidity sensitive section 12 of the sensor 102 will be described with reference to FIGS. 4A to 4E.

Figure 4A:
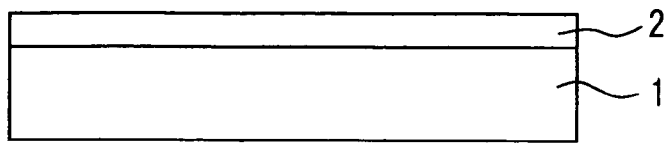
FIGS. 4A to 4E are cross-sectional views showing a manufacturing process of a humidity sensitive section of the sensor in FIG. 1A.

Referring to FIG. 4A, a silicon semiconductor substrate 1 is prepared. An insulating layer 2 made of silicon oxide is formed on the substrate 1. A diffusion layer of a semiconductor element that constructs the circuit section 20a is formed in the substrate 1. The insulating layer 2 is provided as an interlayer insulation layer that is used for forming a wiring of the diffusion layers.

Figure 4B:
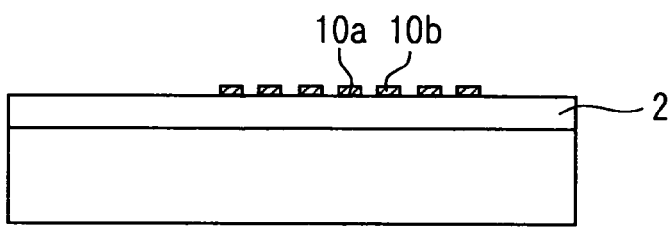

Referring to FIG. 4B, comb electrodes 10a, 10b are formed on the substrate 1 through the insulating layer 2, after an anneal process is applied to the substrate 1.

Figure 4C:
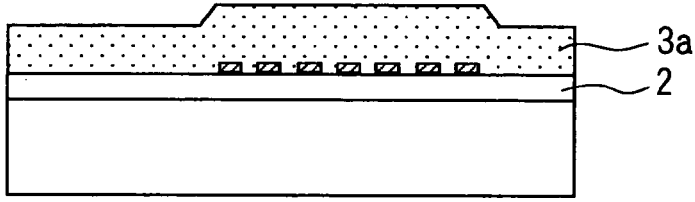

Referring to FIG. 4C, a protective layer 3a is formed on the insulating layer 2, on which the comb electrodes 10a, 10b are formed. The protective layer 3a is made of silicon oxide or silicon nitride, for example. The protective layer 3a can be formed in a process where a protective layer covering the substrate 1 including the wiring of the semiconductor element is formed. In this case, manufacturing cost of the sensor 102 can be reduced.

Figure 4D:
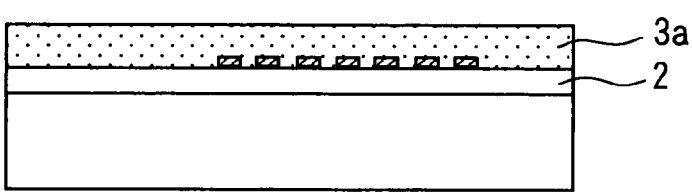

Referring to FIG. 4D, a surface of the protective layer 3a can be made flat by Chemical Mechanical Polishing (CMP), for example.

Figure 4E:
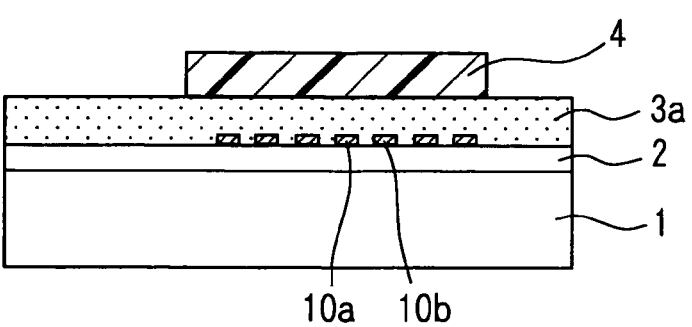

Referring to FIG. 4E, a humidity sensitive layer 4 is formed on the protective layer 3a. An interface between the protective layer 3a and the humidity sensitive layer 4 becomes flat because of the planarized surface of the protective layer 3a.

Thus, the humidity sensitive section 12 of the sensor 102 is formed through the steps shown in FIGS. 4A to 4E.

Although the present invention has been fully described in connection with the preferred embodiments thereof with reference to the accompanying drawings, it is to be noted that various changes and modifications will become apparent to those skilled in the art.

For example, in the sensors 101, 102 of the above-described embodiments, the other parts except for the humidity sensitive section 12 can be suitably changed without being limited to those.

Such changes and modifications are to be understood as being within the scope of the present invention as defined by the appended claims.

What is claimed is:

1. A method of manufacturing a capacitive humidity sensor comprising:
    forming a pair of comb electrodes arranged on a surface of a semiconductor substrate to face with each other with a predetermined gap;
    forming a protective layer to protect the comb electrodes; and
    forming a humidity sensitive layer which contacts a surface of the protective layer and covers the comb electrodes through the protective layer, wherein
    the forming of the protective layer includes a step of polishing the surface of the protective layer to be flat, and
    the comb electrodes are formed while a wiring for a semiconductor element, which is located at a different position of the substrate from the comb electrodes, is formed.

2. The method according to claim 1, further comprising: forming an insulating layer on the surface of the semiconductor substrate, wherein the comb electrodes are formed on the insulating layer.

3. The method according to claim 1, wherein the protective layer is formed while a protective layer for protecting a wiring for a semiconductor element, which is disposed on a different position of the substrate from the comb electrodes, is formed.

4. The method according to claim 1, wherein the comb electrodes are made of aluminum or aluminum alloy.

5. The method according to claim 1, wherein the protective layer is made of silicon oxide, silicon nitride, or a laminated member of a silicon oxide layer and a silicon nitride layer.

6. The method according to claim 1, wherein the humidity sensitive layer is made of polyimide resin.

7. The method according to claim 1, wherein the protective layer is formed such that the humidity sensitive layer is out of contact with the comb electrodes.

8. A method of manufacturing a capacitive humidity sensor comprising:
    forming an insulating layer on a surface of a semiconductor substrate;
    forming a pair of comb electrodes to be embedded in the insulating layer so as to form a flat surface;
    forming a protective layer on the flat surface to protect the comb electrodes; and
    forming a humidity sensitive layer which covers the comb electrodes through the protective layer,
    wherein the comb electrodes are formed while a wiring for a semiconductor element, which is located at a different position of the substrate from the comb electrodes, is formed.

9. The method according to claim 8, wherein the protective layer is formed while a protective layer for protecting a wiring for a semiconductor element, which is disposed on a different position of the substrate from the comb electrodes, is formed.

10. The method according to claim 8, wherein the protective layer is formed such that the humidity sensitive layer is not contact with the comb electrodes.

11. A method of manufacturing a capacitive humidity sensor comprising:
    forming an insulating layer on a surface of a semiconductor substrate;
    forming a pair of comb grooves on a surface of the insulating layer;
    forming a pair of comb electrodes by filling the pair of comb grooves with an electrically conductive material;
    planarizing the surface of the insulating layer after the pair of comb electrodes is formed;
    forming a protective layer on the planarized surface of the insulating layer to directly cover the pair of comb electrodes; and
    forming a humidity sensitive layer on the protective layer to cover the pair of comb electrodes through the protective layer,
    wherein the protective layer is formed such that the pair of comb electrodes is out of contact with the humidity sensitive layer.

* * * * *